US00PP11577P

United States Patent [19]

Meilland

[11] Patent Number: Plant 11,577

[45] Date of Patent: Oct. 17, 2000

[54] GROUND COVER ROSE PLANT NAMED 'MEIVAHYN'

[75] Inventor: Alain A. Meilland, Antibes, France

[73] Assignee: CP (Delaware), Inc., Wilmington, Del.

[21] Appl. No.: 09/150,169

[22] Filed: Sep. 9, 1998

[51] Int. Cl.[7] ..... A01H 5/00

[52] U.S. Cl. ..... Plt./103

[58] Field of Search ..... Plt./101, 103, 104, Plt./107, 144

*Primary Examiner*—Howard J. Locker

*Attorney, Agent, or Firm*—Burns, Doane, Swecker & Mathis, L.L.P.

[57] ABSTRACT

A new and distinct variety of ground cover rose plant (i.e., garden rose plant) is provided which forms in abundance on a substantially continuous basis attractive semi-double blossoms that are white in coloration. The bud coloration is Empire Yellow suffused with very light red. The vegetation is vigorous and the growth habit is broad. Attractive ornamental medium green and semi-glossy foliage is formed. Very good disease resistance is exhibited. Additionally, the new variety grows very well on its own roots following asexual reproduction by cuttings.

1 Drawing Sheet

SUMMARY OF THE INVENTION

The new variety of *Rosa hybrida* ground cover rose plant of the present invention was created by artificial pollination wherein two parents were crossed which previously had been studied in the hope that they would contribute the desired characteristics. The female parent (i.e., the seed parent) of the new variety was the 'Katharina Zeimet' variety (non-patented in the United States). The male parent (i.e., the pollen parent) of the new variety was the product of the cross between the 'Korbin' variety (non-patented in the United States) and the 'Meicoublan' variety (U.S. Plant Pat. No. 6,088). The parentage of the new variety can be summarized as follows:

'Katharina Zeimet'×('Korbin'×'Meicoublan').

The seeds resulting from the above pollination were sown and small plants were obtained which were physically and biologically different from each other. Selective study resulted in the identification of a single plant of the new variety.

It was found that the new variety of ground cover rose plant of the present invention possesses the following combination of characteristics:

(a) abundantly and substantially continuously forms attractive semi-double blossoms that are white in coloration,
(b) exhibits a broad growth habit,
(c) forms vigorous vegetation,
(d) forms attractive ornamental medium green semi-glossy foliage,
(e) propagates well by cuttings, and
(f) exhibits very good disease resistance with respect to black spot and powdery mildew.

The new variety of the present invention can be readily distinguished from its parent varieties. For instance, the 'Katharina Zeimet' variety displays a dwarf bushy growth habit with small flowers. The 'Korbin' variety is of the Floribunda type and displays an upright growth habit with semi-double flowers. The 'Meicoublan' variety displays a ground cover growth habit combined with large pure white very double flowers.

The new variety well meets the needs of the horticultural industry. It can be grown to advantage as attractive ornamentation in parks, gardens, public areas, and residential landscapes. Accordingly, it is particulary well suited for growing in the landscape. The white blossoms contrast nicely with the dark green semi-glossy foliage.

The characteristics of the new variety have been found to be homogeneous and stable and are strictly transmissible by asexual propagation conducted at LeCannet-des-Maures, Var, France such as budding, grafting, and cuttage from one generation to another. The plant propagates well and grows very well on its own roots when propagated from cuttings.

The new variety has been named the 'Meivahyn' variety.

BRIEF DESCRIPTION OF THE PHOTOGRAPH

The accompanying photograph shows, as nearly true as it is reasonably possible to make the same in a color illustration of this character, typical specimens of the plant and plant parts of the new variety. The rose plants of the new variety illustrated herein were two years of age and were grown outdoors during September on their own roots at LeCannet-des-Maures, Var, France. Dimensions in centimeters are indicated at the bottom of the photograph.

FIG. 1—illustrates a specimen of a young shoot;

FIG. 2 —illustrates a specimen of a floral bud before the opening of the sepals;

FIG. 3 —illustrates a specimen of a floral bud at the opening of the sepals;

FIG. 4 —illustrates a specimen of a floral bud at the opening of the petals;

FIG. 5 —illustrates a specimen of a flower in the course of opening;

FIG. 6 —illustrates a specimen of an open flower —plan view —obverse;

FIG. 7 —illustrates a specimen of an open flower —plan view —reverse;

FIG. 8 —illustrates a specimen of a fully open flower —plan view —obverse;

FIG. 9 —illustrates a specimen of a fully open flower —plan view —reverse;

FIG. 10 —illustrates a specimen of a floral receptacle showing the arrangement of the stamens and pistils;

FIG. 11 —illustrates a specimen of a floral receptacle showing the arrangement of the pistils (stamens removed);

FIG. 12 —illustrates a specimen of a flowering stem;

FIG. 13 —illustrates a specimen of a main branch;

FIG. 14 —illustrates specimens of leaves with three leaflets —plan view —upper surface (top) and under surface (bottom);

FIG. 15 —illustrates a specimen of a leaf with five leaflets —plan view —upper surface;

FIG. 16 —illustrates a specimen of a leaf with seven leaflets —plan view — under surface; and FIG. 17 —illustrates a specimen of a leaf with nine leaflets —plan view —upper surface.

DETAILED DESCRIPTION

Figures 1, 2, 3, 4, 5, 6, 7, 8, 9, 10, 11, 12, 13, 14, 15, 16, 17:
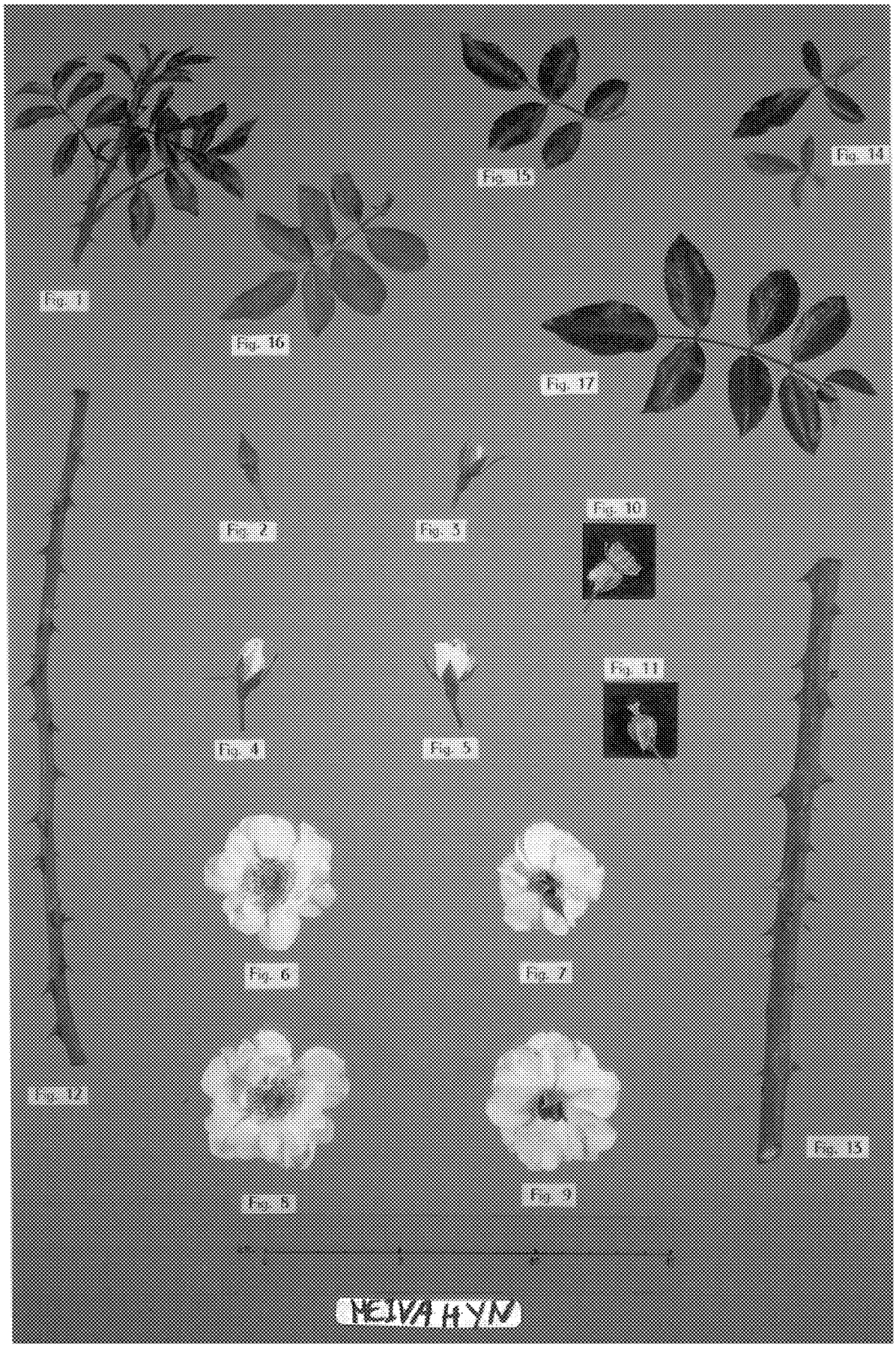

The chart used in the identification of colors is that of The Royal Horticultural Society (R.H.S. Colour Chart). The terminology which precedes reference to the chart has been added to indicate the corresponding color in more common terms. The description is based on two year-old specimens of the new variety during October while grown outdoors on their own roots at LeCannet-des-Maures, Var, France.

Class: Ground cover (garden rose).

Plant:

*Height.*—Approximately 50 to 60 cm. on average at the end of the growing season.

*Width.*—Approximately 110 to 120 cm. on average at the end of the growing season.

*Habit.*—Broad ground cover.

Branches:

*Color.*—Young stems: Near Yellow-Green Group 146C and suffused with yellow brown. Adult wood: Near Yellow-Green Group 146C.

*Thorns.*—Size: Medium (as illustrated). Quantity: Medium (as illustrated). Color: Reddish on young stems and Havana brown on adult wood (Greyed-Orange Group 166A to 166D.

Leaves:

*Stipules.*—Adnate, pectinate, and relatively wide.

*Petioles.*—Upper surface: Medium green (Green Group 137B to 137C) and striped reddish on young foliage and more or less glandular. Under surface: Light green with a few prickles.

*Leaflets.*—Number: 3,5,7 (most often), 9. Shape: Lanceolate. Size: Medium. Serration: Simple and regular. Texture: Consistent. Overall appearance: Very dense, and medium green in coloration, with some glossiness. Color (young foliage): Upper surface: Near Yellow-Green Group 146A. Under surface: Near Yellow-Green Group 146C. Color (adult foliage): Upper surface: Near Yellow-Green Group 146A. Under surface: Near Yellow-Green Group 146B.

Inflorescence:

*Number of flowers.*—Commonly approximately 6 to 15 blooms per floral stem.

*Peduncle.*—Short and light green (Green Group 144A) with prickles, and approximately 2.5 cm. in length on average.

*Sepals.*—Upper surface: Near Green Group 138A in coloration. Under surface: Near Green Group 138A in coloration.

*Buds.*—Shape: Conical. Length: Approximately 1.5 cm. on average. Size: Small. Color (when opening): Upper surface: Near Empire Yellow, Yellow Group 11D, and widely suffused with Red Group 56D. Under surface: New Empire Yellow, Yellow Group 11D, and widely suffused with Red Group 56D.

*Flower.*—Form: Somewhat flattened, and semi-double. Diameter: Approximately 5 cm. on average. Color (when opening begins): Upper surface: Near White Group 155B and lightly suffused with Reg Group 36D. Under surface: Near White Group 155B and lightly suffused with Red Group 36D. Color (when blooming): Upper surface: Near White Group 155B. Under surface: Near White Group 155B. Color (at end of blooming): Upper surface: Near White Group 155B. Under surface: Near White Group 155B. Fragrance: None. Petal form: Possess undulated margins, somewhat rounded on the tip (as illustrated) and obtuse at the base. Petal number: Approximately 21 on average. Stamen number: Approximately 75 on average. Anthers: Ochre in coloration. Filaments: Ochre in coloration. Pistils: Approximately 30 on average. Stigmas: Ochre in coloration. Styles: Greenish in coloration. Stamen number: Approximately 75 on average. Stamen color: Ochre in coloration. Lasting quality: The blossoms commonly last approximately 5 to 7 days on the plant and when cut and placed in a vase. Receptacle: Light green in coloration, and in longitudinal section it is in the shape of a pitcher. Hips: Commonly are formed in medium quantity, approximately 1 cm. in size and near Orange-Red Group 35A to near Red Group 42B in coloration.

Development:

*Vegetation.*—Strong.

*Blossoming.*—Abundant and substantially continuous.

*Resistance to diseases.*—Very good with respect to black spot and powdery mildew.

*Hardiness.*—Has well withstood temperatures of –10° F. in U.S.D.A. Hardiness Zone No. 5.

I claim:

1. A new and distinct variety of ground cover rose plant characterized by the following combination of characteristics:

(a) abundantly and substantially continuously forms attractive semi-double blossoms that are white in coloration,
(b) exhibits a broad growth habit,
(c) forms vigorous vegetation,
(d) forms attractive ornamental medium green semi-glossy foliage,
(e) propagates well by cuttings, and
(f) exhibits very good disease resistance with respect to black spot and powdery mildew;

substantially as herein shown and described.

* * * * *